United States Patent [19]

Weiner et al.

[11] Patent Number: 5,366,958
[45] Date of Patent: Nov. 22, 1994

[54] LOCALIZED DELIVERY USING FIBRONECTIN CONJUGATES

[75] Inventors: Alan L. Weiner, Plainsboro; Robert P. Lenk, Lambertville; Sharon S. Carpenter-Green, Cranbury; Michael W. Fountain, Plainsboro, all of N.J.

[73] Assignee: The Liposome Company, Inc., Princeton, N.J.

[21] Appl. No.: 110,193

[22] Filed: Aug. 20, 1993

Related U.S. Application Data

[63] Continuation of Ser. No. 611,336, Nov. 9, 1990, abandoned, which is a continuation of Ser. No. 533,583, Sep. 19, 1983, abandoned.

[51] Int. Cl.$^5$ .................. A61K 37/02; A61K 9/127; A61K 9/133; C07K 7/02
[52] U.S. Cl. .......................... 514/2; 424/450; 530/380; 530/810; 530/812
[58] Field of Search ............... 424/450; 530/380, 810, 530/812; 514/2

[56] References Cited

U.S. PATENT DOCUMENTS 4,193,983  3/1980  Ullman et al. .................. 424/11
4,235,871  11/1980  Papahadjapalos et al. ........... 424/19

FOREIGN PATENT DOCUMENTS 2712031  9/1977  Germany .

OTHER PUBLICATIONS

Anderson et al., 1964, J. Am. Chem. Soc. 86:1839–1842.
Bangham et al., 1965, J. Mol. Biol. 13:238–252.
Chazov et al., 1981, Proc. Natl. Acad. Sci. USA 78:5603–5607.
Hague and Kito, 1982, Agric. Biol. Chem. 46:597–599.
Hsu and Juliano, 1982, Biochim. Biophys. Acta, 1982, 720:411–419.
Huang et al., 1980, J. Biol. Chem. 255:8015–8018.
Huang et al., 1982, Biochem. Biophys. Acta, 716:140–150.
Jilek and Hörmann, 1977, Hoppe-Seyler's Z. Physiol. Chem. 358:1165–1168.
Juliano and Stamp, 1976, Nature 261:235–238.
Lenk et al., 1982, Eur. J. Biochem. 121:475–482.
Leserman et al., 1979, J. of Immunology 122:585–591.
Martin et al., 1981, Biochemistry 20:4229–4238.
Martin and Papahadjopoulos, 1982, J. Biol. Chem. 257:286–288.
Mayhew and Papahadjopoulos, 1983, Liposomes, Ostro ed., Marcel Dekker, Inc., 289–341.
Mosher, 1975, J. of Biol. Chem. 250:6614–6621.
Mosher and Proctor, 1980, Science 209:927–929.
Mosher et al., 1980, J. Biol. Chem. 255:1181–1188.
Nishida et al., Aug. 27, 1983, The Lancet, 521–522.
Phillips et al., 1979, Annals of the Rheum. Dis. 38:553–557.
Rossi and Wallace, 1983, J. Biol. Chem. 258:3327–3331.
Shaw et al., 1978, Ann. N.Y. Acad. Sci. 308:435–436.
Shen et al., 1982, Biochem. Biophys. Acta 689:31–37.
Weissmann et al., 1975, Proc. Natl. Acad. Sci. USA 72:88–92.
Wu et al., 1981, Biochem. Biophys. Acta 674:19–29.
Wu et al., 1981, Proc. Natl. Acad. Sci. USA 78:2033–2037.
Yamada, 1981, Cell Biology of the Extracellular Matrix, Hay ed., Plenum Press, 95–114.

*Primary Examiner*—Jacqueline Stone
*Attorney, Agent, or Firm*—Allen Bloom; Joanne Longo Feeney

[57] ABSTRACT

This invention encompasses new and substantially improved methods and compositions for delivery of therapeutic agents to specifically chosen body sites. Conjugation of fibronectin to bioactive agents or to lipids or to liposomes which entrap the bioactive agents permits immobilization of the bioactive agent when administered at collagen-, heparin-, hyaluronic acid-, fibrin/fibrinogen-, or ganglioside-rich sites. Covalent conjugation is achieved by two methods: (1) the enzymatically catalyzed cross-linkage of fibronectin to an amine containing compound, and (2) by a modified NHS method which permits formation of peptide bonds between fibronectin and lipid compounds.

25 Claims, No Drawings

LOCALIZED DELIVERY USING FIBRONECTIN CONJUGATES

This application is a continuation of copending application Ser. No. 07/611,336 filed on Nov. 9, 1990, now abandoned, which is a continuation of Ser. No. 06/533,583, filed Sep. 19, 1983, now abandoned.

1. FIELD OF THE INVENTION

This invention relates to methods and compositions which are used to enhance retention of administered bioactive agents at specific tissue or organ sites in the body of man or animals. The present invention involves covalent linkage of fibronectin to bioactive agents or their carriers to form conjugates having high affinity for collagen-, heparin-, fibrin/fibrinogen-, hyaluronic acid-, or ganglioside-rich body sites.

Methods and compositions described herein have a wide range of applicability to the field of drug delivery systems. The practice of the present invention is demonstrated herein by way of example for the localized delivery of medicament to joints by intra-articular administration of the medicament entrapped in liposomes with enhanced affinity for joints conferred by fibronectin covalently cross-linked to the lipid bilayer.

2. BACKGROUND OF THE INVENTION

2.1. TARGETED AND LOCALIZED DRUG DELIVERY SYSTEMS

In order to exert characteristic therapeutic effects an administered drug must reach the proper site of action at an appropriate concentration. Thus, desirable features of drug delivery systems include resistance to rapid clearance and sustained release of drug at its site of activity. Another desirable feature is the ability to deliver the drug to a specific site of intended action without adversely affecting non-target tissues or systems. This latter feature is especially important when administering drugs such as anti-tumor agents which are particularly toxic, or drugs such as local anesthetics or steroid hormones which may have undesirable systemic side effects.

Although much has been written regarding the potential advantages of lipid vesicles or liposomes as in vivo drug delivery systems, failure to deliver drug to a specific site of activity continues to be a serious drawback (see review by Mayhew and Papahadjopoulos, 1983, "Therapeutic Applications of Liposomes" in *Liposomes*, Ostro, ed., Marcel Dekker, Inc., pp. 289-341).

Administration of targeted liposome preparations (liposomes designed to "home" to specific tissue or cell sites upon application in vivo) has been attempted by a number of researchers. Liposomes bearing substances such as antigenic lipids, i.e., N-dinitrophenylaminocaproyl phosphatidylethanolamine (Lesserman et al., 1979, J. Immunol. 122: 585-591), heat-aggregated IgM molecules (Weissman et al., 1975, Proc. Natl. Acad. Sci. U.S.A. 72: 88-92), and sialoglycoprotein which binds lectins (Juliano and Stamp, 1976, Nature (London) 261:235-238)) have been used in vitro to enhance specific binding to cell surfaces. Huang et al., 1980, J. Bill. Chem. 255:8015-8018, demonstrated specific binding of liposomes to mouse L-929 cells in vitro by incorporation of anti-H-2-monoclonal antibody linked to palmitic acid into the lipid bilayer. More recently, Martin and Papahadjopoulos have demonstrated targeting of liposome preparations by the covalent linkage of Fab' fragments via disulfide bonds to a derivative of phosphatidylethanolamine incorporated into the lipid bilayer (1982, J. Biol. Chem. 257:286-288; Martin, Hubbell and Papahadjopoulos, 1981, Biochem. 20:4229-4238).

The use of of liposome preparations for localized drug delivery has also been attempted. In the liposome preparations which are designed to adhere at the site of administration, enhanced affinity is conferred by means of "stick" adjuvants. Liposomes with synthetic aminosaccharide compounds conjugated to cholesterol incorporated into the lipid bilayer have been shown to have enhanced affinity for cells or tissues when extravascularly applied by subcutaneous administration (Wu et al., 1981, Biochim. Biophys. Acta 674:19-29; Wu et al., 1981, Proc. Natl. Acad. Sci., U.S.A. 78:2033-2037).

Localized drug delivery has also been attempted by utilization of specific routes of administration. For example localized administration of steroid (cortisol palmirate) entrapped in dipalmitoylphosphatidylcholine liposomes by means of intra-articular administration to joints has been demonstrated to have superior anti-inflammatory activity compared to administration of free steroid (Shaw et al., 1978, Ann. N.Y. Acad. Sci. 308: 435-436; Philips et al., 1979, Ann. Rheum. Dis. 38: 553-557).

2.2. FIBRONECTIN

Plasma fibronectin, also called cold insoluble globulin (CIG) or large external transformation sensitive (LETS) protein, is a dimeric glycoprotein of approximately 440,000 daltons molecular weight. The polypeptide chains of the dimer are linked by disulfide bonds. Fibronectin binds to a number of naturally occurring substrates including collagen/gelatin, heparin, hyaluronic acid, fibrin/fibrinogen, transglutaminase substrates, gangliosides, cells, bacteria, actin and DNA. (See Yamada, 1981, "Fibronectin and Other Structural Proteins" in *Cell Biology of the Extracellular Matrix*, Hay, ed., Plenum Press, pp. 95-114).

Fibronectin has been cross-linked to collagen and various amines including dansylcadaverine, spermine, spermidine, and putresane, and bacterial cell membranes by Factor XIII or transglutaminase enzyme (Mosher and Proctor, 1980, Science 209:927-929; Mosher et al., 1980, J. Biol. Chem. 255:1181-1188; Mosher, 1975, J. Biol. Chem. 250:6614-6621). Transglutaminase, a calcium dependent enzyme, catalyzes an acyl transfer reaction in which gamma-carboxamide groups of glutamyl residues are acyl donors and primary amines are acyl acceptors. Thus, transglutaminase forms epsilon-gamma glutamyl-lysine linkages between proteins.

Although several studies have suggested the utilization of fibronectin non-covalently bound to phospholipid vesicles as a possible means of targeting liposomes to particular body sites rich in collagen (see Ross and Wallace, 1983, J. Biol. Chem. 258:3327-3331; Chazon et al., 1981, Proc. Natl. Acad. Sci., U.S.A. 78:5603-5607) no study to date has demonstrated such specific targeting in vivo. Hsu and Juliano, 1982, Biochim. Biophys. Acta 720:411-419, have demonstrated enhanced adherence of liposomes coated with fibronectin (by a non-covalent association) to macrophages in vitro. While such preparations may be useful to treat intracellular infections of the reticuloendothelial system, the liposomes would presumably be cleared rapidly from the circulation. Moreover, the non-covalently attached fibronectin-lipid associations suffer from several disadvantages. Such associations are unstable, and the amount of fibronectin associated cannot easily be controlled.

2.3. N-HYDROXYSUCCINIMIDE METHOD OF CONJUGATION

Activated esters of N-hydroxysuccinimide (NHS) have long been used to form peptide linkages between free carboxyl groups and primary amines. (Anderson et al., 1964, J. Am. Chem. Soc. 86:1839–1842).

Huang et al. utilized an activated ester of palmitic acid and NHS to form a conjugate of palmitic acid and monoclonal anti-H-2 antibody which was then incorporated into liposome bilayers. (1980, J. Biol. Chem. 255: 8015–8018). Peptide linkage between the antibody and palmitic acid was performed in the presence of detergent (deoxycholate) in order to solubilize the lipid which would precipitate in an aqueous buffer. Formation of liposomes with antibody conjugate incorporated was accomplished by dialysis to remove detergent.

Recently this group of investigators has incorporated this derivatized palmitoyl-antibody into liposomes by mixing the derivatized antibody in detergent with preformed liposomes made by a modified reverse evaporation method (Shen et al., 1982, Biochim. Biophys. Acta 689:31–37). A high level of attachment of antibody, capable of binding to antigen, was achieved without inducing leakage of vesicles; however, a lengthy, 40-hour dialysis was necessary to remove the detergent. (See also, Huang et al., 1982, Biochim. Biophys. Acta 716:140–150). Although these liposomes could be shown to adhere to cells in vitro, targeting in vivo may be obscured by removal of vesicles by the reticuloendothelial system.

The covalent attachment of long chain fatty acids to the hydrophilic soybean protein glycinin was reported by Haque and Kito (1982, Agric. Biol. Chem. 46(2):597–599). Active NHS esters of lipids were reacted with glycinin in a reaction buffer consisting of tetrahydrofuran (THF) and 8M urea. The conjugated product in solution was dialyzed exhaustively for three days against deionized water to remove THF before freeze-drying.

3. SUMMARY OF THE INVENTION

This invention presents new and substantially improved compositions and methods for enhancing localized retention of administered bioactive agents at specific sites in vivo which are rich in collagen, heparin, hyaluronic acid, fibrin/fibrinogen, gangliosides, or transglutaminase substrates. The invention is based upon the fact that fibronectin has a strong affinity for such sites in vivo. When fibronectin is covalently linked to a bioactive agent or to its carrier, the affinity of the resulting conjugate for appropriate sites in vivo is greatly increased. For example, enhanced affinity for collagenous sites is conferred by the covalent binding of fibronectin to a bioactive agent or to its carrier (e.g., the liposome in which the bioactive agent is entrapped).

According to the present invention, fibronectin conjugates are prepared by either of two methods. According to one method, thrombin-activated calcium-dependent Factor XIII, or transglutaminase enzyme, is used to crosslink fibronectin to a number of substrates containing a plurality of amines; such substrates include but are not limited to lipids which are incorporated within a liposome, peptides, proteins, aminoglycoside antibiotics, etc. A second method entails a substantially improved modification of the N-hydroxysuccinimide (NHS) protocol for formation of peptide bonds between fibronectin and lipid compounds.

In order to effect localized delivery in vivo, conjugates of the present invention may be administered directly to the site in vivo or may first be incorporated into liposome preparations which provide sustained release of entrapped medicament. Covalent linkage of the fibronectin to lipid is essential for stability of liposomes containing fibronectin. The fibronectin conjugates described herein offer the following advantages:

(1) they adhere to body sites rich in collagen, fibrin/fibrinogen, hyaluronic acid, heparin, transglutaminase substrates, actin, etc.;

(2) they reduce systemic side effects by localizing medicament at the site of administration; and (3) they concentrate medicament at the site of action.

As a result, these conjugates overcome problems of rapid clearance and non-specificity associated with conventional drug delivery systems.

4. DETAILED DESCRIPTION OF THE INVENTION

The present invention involves methods and formulations of conjugates of fibronectin (i.e., fibronectin covalently bound to amine-containing compounds such as lipids, peptide hormones, proteins, or aminoglycosides or to carboxyl-containing lipids such as fatty acids, acidic phospholipids, derivatized phospholipids or liposomes) which have numerous advantages for use as drug delivery or carrier systems. Fibronectin covalently bound to bioactive agents may be administered directly or incorporated into a liposome preparation which is then administered in vivo. Alternatively, if fibronectin is bound to a lipid, this conjugate may be incorporated into the lipid bilayer of liposomes containing an entrapped bioactive agent.

The following sections describe how the conjugates are prepared and used.

4.1 ENZYMATIC PREPARATION OF FIBRONECTIN CONJUGATES

Fibronectin can be obtained from the fibrinogen fraction of vertebrate blood, and is commercially available as lyophilized preparations. Rather than using commercially available fibronectin, it is possible to isolate naturally occurring substance from the plasma of an intended recipient and, after appropriate purification, administer the same, thereby minimizing the possibility of immune reactions.

According to one embodiment of the present invention, conjugation of fibronectin to compounds containing a plurality of amines may be achieved by the enzymatically catalyzed cross-linkage of the glutamine of the N-terminus of the fibronectin glycoprotein to the compound.

Blood coagulation Factor XIII or transglutaminase, a calcium dependent enzyme, has been demonstrated to crosslink fibronectin (via glutamyl residues) to various amine containing substrates such as bacterial membranes (Mohser and Proctor, 1980, Science 209:927–929); polyamines such as putrescine, spermidine, spermine, dansylcadaverine, N-(5-aminopentyl)-5-dimethylamino-naphthalene-1 sulfonamide (Mosher et al. 1980, J. Biol. Chem. 255:1181–1188; 1977, Hoppe- Seyler's Z. Physiol. Chem. Bd. 358:1165–1168); and to fibronectin itself (Mosher, 1975, J. Biol. Chem. 250:6614–6621).

Factor XIII is utilized in the present invention to catalyze the crosslinking of fibronectin to a number of substrates. Presumably the crosslinking occurs via an acyl transfer reaction in which the gamma-carboxamide group(s) of peptide-bound glutamyl residue(s) of fibronectin function as acyl donors. Substrates containing a plurality of amines function as acyl acceptors. These substrates include but are not limited to: lipids, such as phosphatidylethanolamine, phosphatidylserine, etc. which are incorporated into liposome membranes; proteins such as fibrinogen, etc.; peptide hormones such as somatotropin or growth hormone, luteinizing hormone, etc.; aminoglycosides such as gentamicin, neomycin, tobramycin, and kanamycin, etc. Thus, fibronectin may be conjugated directly to a lipid molecule which is incorporated into a liposome or to a bioactive agent. It should be noted that the transglutaminase catalyzed reaction is carried out in an aqueous buffer; therefore, lipid substrates (which are not soluble in aqueous solutions) must be incorporated into liposomes in order to function as the enzyme substrate in the aqueous reaction mixture.

Fibronectin-liposome conjugates of the present invention may be prepared using the following protocol: liposomes, prepared as described herein (Section 4.3.) using egg phosphatidylcholine (EPC) and between 0.5 to 40 mole % phosphatidylethanolamine (PE) (e.g., 3.71 mg PE) are incubated at room temperature for 2 hours with greater than 0.3 mg (e.g., 0.65 mg) fibronectin, 20 to 200 ug Factor XIII (transglutaminase), and at least 1 unit Thrombin (range 1 to 10 units) in 5 to 50 mM $CaCl_2 \cdot 6H_2O$ (one unit thrombin will clot a 250 mg % fibrinogen solution in 15 seconds at 37° C.). As a result the fibronectin is covalently linked to the PE which is incorporated into the liposome bilayer.

According to one embodiment of the present invention, enzyme catalyzed cross-linkage of fibronectin to stable plurilamellar lipid vesicles (SPLVs prepared as described infra) was effected using a number of formulations. Formulation 1: SPLV-entrapped streptomycin (control SPLVs) was prepared using 100 mg EPC and 100 mg streptomycin sulfate; Formulation 2: control SPLVs were prepared except 0.65 mg fibronectin was added externally to the lipid ingredients in order to non-covalently associate with the liposomes; Formulation 3: control SPLVs were incubated with 0.65 mg FN, 90 ug Factor XIII, 1 unit Thrombin in 20 mM $CaCl_2 \cdot 6H_2O$; Formulation 4: SPLV-entrapped streptomycin, prepared using 100 mg EPC, 3.71 mg phosphatidylethanolamine (PE), and 100 mg streptomycin sulfate was incubated with 0.65 mg FN, between 90 to 100 ug Factor XIII, 1 unit Thrombin in 20 mM $CaCl_2 \cdot 6H_2O$ in order to covalently attach the fibronectin to the lipid bilayer. In all cases a trace amount of $^{125}$I-p-hyroxyphenylpropionic acid derivatized gentamicin sulfate ($^{125}$I-GS) was incorporated as radiolabel. All preparations were incubated at room temperature for 2 hours, centrifuged at 15,000×g for 10 minutes, and washed 2 times in PBS. Aliquots of the FN-modified SPLVs were applied to collagen Sepharose columns (prepared as described below) to determine binding of fibronectin-modified vesicles.

The following collagen or gelatin Sepharose assay system was developed to measure the affinity of FN-modified SPLVs for collagen: 5 gm of cyanogen bromide activated Sepharose 4B was washed on a glass filter with 1 liter of 1 mM HCl to remove dextran/lactose stabilization additives. Fifty mg of gelatin was dissolved with gentle heating in 50–100 ml of coupling buffer containing: 0.1M $NaHCO_3$ and 0.5M NaCl at pH 8.3. The Sepharose was washed in coupling buffer and mixed with the cooled gelatin mixture. After 2 hours incubation at room temperature (with mechanical shaking), the unbound gelatin was washed away with coupling buffer. The remaining active groups were reacted with 100 ml of blocking groups (either 0.2M glycine at pH 8 or 1M ethanolamine at pH 8) for 1–2 hours. Three washing cycles were used each consisting of wash with acetate buffer (0.1M sodium acetate plus 1M NaCl at pH 4), followed by bicarbonate buffer wash (0.1M $NaHCO_3$ plus 1M NaCl pH 8.3).

FN-modified SPLVs migrated into the collagen column whereas liposomes without FN did not, thus indicating successful attachment of the fibronectin to the SPLVs. Radiolabel entrapped in the FN-modified SPLVs could be eluted in significant amounts only with 8M urea.

Sodium dodecylsulfate polyacrylamide gel electrophoresis (SDS-PAGE) of fibronectin-modified liposomes demonstrated that covalent cross linkage of fibronectin to the lipid bilayer was essential for prolonged stability of vesicle preparations. One month after SPLVs were prepared lipids were extracted and protein was precipitated using ethanol-chloroform (9:1). When applied to 7.5% SDS polyacrylamide gels only preparations of SPLVs with fibronectin covalently attached (i.e., SPLVs incubated with fibronectin and Factor XIII; or SPLVs incubated with fibronectin, Factor XIII, and thrombin) demonstrated the characteristic fibronectin band of about 200,000 daltons molecular weight. SPLVs prepared with fibronectin non-covalently associated (i.e., SPLVs incubated with fibronectin but no enzyme) did not exhibit this banding, indicating dissociation of the fibronectin-lipid complex and possible breakdown of the fibronectin molecule itself. Thus, for stable liposome preparations with enhanced affinity for collagen-rich areas it is desirable to covalently cross-link the fibronectin to the lipid.

4.2. PREPARATION OF FIBRONECTIN CONJUGATES BY A MODIFIED NHS METHOD

According to another embodiment of the present invention, fatty acids, acidic phospholipids such as phosphatidic acid or phosphatidylserine, derivatized phospholipids or liposomes may be conjugated with fibronectin using a modified NHS procedure. These fibronectin-lipid conjugates may then be incorporated into liposomes for therapeutic use.

Procedures for this modified NHS method of conjugate preparation are disclosed in U.S. Patent Application by Robert P. Lenk, Sharon S. Carpenter-Green, Alan L. Weiner, and Michael W. Fountain entitled "Improved Methods For Conjugate Formation Using N-hydroxysuccinimide Lipid Esters" filed concurrently herewith now abandoned.

In an N-hydroxysuccinimide reaction, dicyclohexylcarbodiimide is utilized to activate a free carboxyl group on the lipid molecule and effect an activated ester linkage with the amine groups of NHS in order to form a reactive intermediate (NHS-lipid intermediate). For example, the intermediate composed of either NHS-fatty acid or NHS-phospholipid ester is prepared by incubation of dicyclohexylcarbodiimide, NHS, and either a fatty acid or phospholipid at room temperature for several hours. When fibronectin is added to the reaction mixture containing the NHS-lipid intermediate, the fibronectin-lipid conjugate is formed.

The conventional reaction mixture used to make lipid conjugates is an emulsion of the NHS-lipid intermediate and the protein prepared using detergent in an aqueous environment. In contrast, the reaction solutions of the present invention comprise approximately equal volumes of an organic solvent containing the NHS-lipid ester intermediate and aqueous buffer containing fibronectin (organic-aqueous reaction buffer). The organic solvent must (1) be miscible with aqueous solutions, (2) solubilize the NHS-lipid intermediate, and (3) not denature the fibronectin. Solvents which may be used in the process include but are not limited to dimethylformanide (DMF), tetrahydrofuran (THF), dioxane, and lower number carbon aliphatic alcohols (i.e., not greater than 5 carbon atoms including but not limited to methanol, ethanol, propanol, butanol, pentanol, etc.)

When the reaction in organic-aqueous reaction buffer is complete, a large amount of aqueous buffer is added to the reaction mixture. The unreacted fibronectin will be solubilized by the aqueous buffer and the lipid conjugate and unreacted lipids will precipitate out of solution. The suspension is separated by centrifugation or filtration, and the supernatant or filtrate containing unreacted compound is removed.

Organic solvent is then added to the mixture of conjugate and unreacted lipid in order to solubilize the unreacted lipid, but not the conjugate. Of course, the addition of organic solvent to remove unreacted lipids may precede the addition of aqueous buffer to remove the unreacted fibronectin.

Conjugates of the present invention may be incorporated into the lipid bilayer of liposomes. Incorporation of preformed lipid conjugates may be accomplished either by mixing the lipid conjugate with preformed liposomes, or by adding the conjugate to a mixture of lipids used to prepare the liposomes. Alternatively, NHS-lipid intermediates may be incorporated into the liposome bilayer and fibronectin added to such preparations to form the fibronectin-lipid conjugate covalently attached to the liposome.

In one experiment a liquid phase synthesis was employed to prepare a fibronectin-palmitate conjugate. An NHS-palmitate intermediate was prepared as follows. The reaction mixture composed of: 500 mg NHS dissolved in 15 ml ethyl acetate, 750 mg palmitic acid, and 1.25 ml ethyl acetate containing 773 mg dicyclohexylcarbodiimide was incubated overnight at room temperatures. Following incubation, the solution was filtered (Whatman #1), rotoevaporated to remove ethyl acetate, and redissolved in 40 ml ethanol at 60° C. The solution was then cooled to −20° C., filtered, and the NHS-palmitate crystals thus formed were washed with ice cold ethanol.

The reaction mixture to form the conjugate, composed of 1 mg fibronectin [dialyzed against phosphate buffered saline (PBS)] with trace amount of $^{125}$I-fibronectin as radiolabel in 1 ml PBS and 5 mg NHS-palmitate in 1 ml DMF, was incubated for 30 minutes at room temperature. Following incubation, 5–7 ml Tris-HCl pH 7.4 was added and the suspension was centrifuged at 16,000×g for 30 minutes. The aqueous phase was removed, the insoluble pellet containing the reaction product was redissolved in 2 ml DMF to remove unreacted NHS palmitate, and the mixture was centrifuged again. After washing with Tris-HCl buffer, radioactivity of the remaining pellet was determined. Recovery of 56% of initial $^{125}$I-fibronectin radiolabel as derivatized product indicated that this method affords a rapid, easy and efficient method of covalently linking lipid compounds to fibronectin.

Stable plurilamellar vesicles (SPLVs) were prepared (as described infra using 40 mg egg phosphatidylcholine (EPC). The liposome preparation was then incubated with a trace amount of $^{125}$I-FN-palmitate conjugate for 4–5 hours at 4° C. with shaking in order to form the fibronectin modified SPLVs. Partitioning of the radioactive marker into the SPLVs occurred (60% of the radiolabel was detected in the pelleted liposomes). Aliquots of the fibronectin-modifed SPLVs (FN-SPLVs) were applied to collagen Sepharose columns prepared as previously described. Liposomes containing FN-palmitate in the bilayer migrated into and adhered to collagen columns.

4.3. LIPOSOME PREPARATIONS

According to the present invention, liposome preparations in which fibronectin (FN) constitutes an active component incorporated into the lipid bilayer by the methods described supra may be utilized to provide for enhanced retention of entrapped bioactive agent at the site of administration. While it is possible to use as little as 0.1% fibronectin (by weight of phospholipid in the liposomes), generally the amount will be from 1 to 5%. Upon administration in vivo such liposome compositions are localized to body sites rich in collagen (or elastin), heparin, hyaluronic acid, fibrin/fibrinogen, gangliosides, or transglutaminase substrates due to the affinity of FN for these substances. Various liposome preparations which may be used in the present invention are described in the subsections below.

Liposomes used in the present invention can be prepared by a number of methods, including but not limited to: the original methods of Bangham et al. (1965, J. Mol. Biol. 13: 238–252) which yield multilamellar vesicles (hereinafter MLVs); methods described in U.S. Pat. No. 4,522,803 granted on Jun. 11, 1985 based on U.S. patent application Ser. No. 476,496 filed Mar. 24, 1983 which yield stable plurilamellar vesicles (hereinafter referred to as SPLVs); and methods described in U.S. patent application Ser. No. 521,176 filed August 8, 1983, now U.S. Pat. No. 4,588,578 which yield monophasic vesicles (hereinafter referred to as MPVs). The procedures for the preparation of SPLVs and MPVs are described below.

SPLVs are prepared as follows: an amphipathic lipid or mixture of lipids is dissolved in an organic solvent. Many organic solvents are suitable, but diethyl ether, fluorinated hydrocarbons and mixtures of fluorinated hydrocarbons and ether are preferred. To this solution are added an aqueous phase and the active ingredient to be entrapped. This biphasic mixture is converted to SPLVs by emulsifying the aqueous material within the solvent and evaporating the solvent. Evaporation can be accomplished during or after sonication by any evaporative technique, e.g., evaporation by passing a stream of inert gas over the mixture, by heating, or by vacuum. The volume of solvent used must exceed the aqueous volume by a sufficient amount so that the aqueous material can be completely emulsified in the mixture.

In practice, a minimum of about 3 volumes of solvent to about 1 volume of aqueous phase may be used. In fact, the ratio of solvent to aqueous phase can vary up to 100 or more volumes of solvent to 1 volume aqueous phase. The amount of lipid must be sufficient so as to exceed that amount needed to coat the emulsion droplets (about 40 mg of lipid per ml of aqueous phase). The upper boundary is limited only by the practicality of cost-effectiveness, but SPLVs can be made with 15 gm of lipid per ml of aqueous phase.

Most amphipathic lipids may be constituents of SPLVs. Suitable hydrophilic groups include but are not limited to: phosphato, carboxylic, sulphato and amino groups. Suitable hydrophobic groups include but are not limited to: saturated and unsaturated aliphatic hydrocarbon groups and aliphatic hydrocarbon groups substituted by at least one aromatic and/or cycloaliphatic group. The preferred amphipathic compounds are phospholipids and closely related chemical structures. Examples of these include but are not limited to: lecithin, phosphatidylethanolamine, lysolecithin, lysopnatidylethanolamine, phosphatidylserine, phosphatidylinositol, sphingomyelin, cardiolipin, phosphatidic acid and the cerebrosides. Specific examples of suitable lipids useful in the production of SPLVs are phospholipids which include the natural lecithins (e.g., egg lecithin or soybean lecithin) and synthetic lecithins, such as saturated synthetic lecithins (e.g., dimyristoyl-phosphatidylcholine, or dipalmitoyl-phosphatidylcholine or distearoylphosphatidylcholine) and unsaturated synthetic lecithins (e.g., dioloyl-phosphatidylcholine or dilinoloylphosphatidylcholine. The SPLV bilayers can contain a steroid component such as cholesterol, coprostanol, cholestanol, cholestane and the like. When using compounds with acidic hydrophilic groups (phosphato, sulphato, etc.) the obtained SPLVs will be anionic; with basic groups such as amino, cationic liposomes will be obtained; and with polyethylenoxy or glycol groups neutral liposomes will be obtained. The size of the SPLVs varies widely. The range extends from about 100 nm to about 10,000 nm (10 microns) and usually about 100 nm to about 1,500 nm.

The following is an example of the proportions that may be used in SPLV synthesis: SPLVs may be formed by adding 50 micromoles of phospholipid to 5 ml of diethyl ether containing 5 micrograms of butylatedhydroxytoluene (BHT) and then adding 0.3 ml of aqueous phase containing the active substance to be encapsulated. The resultant solution which comprises the material to be entrapped and the entrapping lipid is sonicated while streaming an inert gas over the mixture thus removing most of the solvent.

See also Lenk et al., 1982, Eur. J. Biochem. 121:475–482 which describes a process for making liposome-encapsulated antibodies by sonicating and evaporating a solution of cholesterol and phosphatidylcholine in a mixture of chloroform and ether with aqueous phase added, but does not set forth the relative proportions of lipid to aqueous phase.

Another suitable liposome preparation which may be used is lipid vesicles prepared in a monophasic solvent system, hereinafter referred to as monophasic vesicles or MPVs. MPVs are particularly stable and have a high entrapment efficiency. MPVs are prepared by a unique process as follows: a lipid or a mixture of lipids and an aqueous component are added to an organic solvent or a combination of organic solvents in amounts sufficient to form a monophase. The solvent or solvents are evaporated until a film forms. Then an appropriate amount of aqueous component is added, and the film is resuspended and agitated in order to form the MPVs.

The organic solvent or combination of solvents used in the process must be (1) miscible with water and (2) once mixed with water should solubilize the lipids used to make the MPVs.

For example, an organic solvent or mixture of solvents which satisfies the following criteria may be used in the process: (1) 5 ml of the organic solvent forms a monophase with 0.2 ml of aqueous component and (2) the lipid or mixture of lipids is soluble in the monophase.

Solvents which may be used include but are not limited to ethanol, acetone, 2-propanol, methanol, tetrahydrofuran, glyme, dioxane, pyridine, diglyme, 1-methyl-2-pyrrolidone, butanol-2, butanol-1, isoamyl alcohol, isopropanol, 2-methoxyethanol, or a combination of chloroform methanol (e.g., in a 1:1 ratio).

The evaporation should be accomplished at suitable temperatures and pressures which maintain the monophase and facilitate the evaporation of the solvents. In fact, the temperatures and pressures chosen are not dependent upon the phase-transition temperature of the lipid used to form the MPVs. The advantage of this latter point is that heat labile products which have desirable properties can be incorporated in MPVs prepared from phospholipids such as distearoylphosphatidylcholine, which can be formed into conventional liposomes only at temperatures above the phase-transition temperature of the phospholipids. The process usually allows more than 30–40% of the available water-soluble material to be entrapped during evaporation and 2–15% of the available water-soluble material to be entrapped during the resuspension; and up to 70–80% of the available lipid-soluble material can be entrapped if the lipid:drug ratio is increased significantly. With MLVs the entrapment of aqueous phase, which only occurs during the rehydration step since no aqueous phase is present during the drying step, usually does not exceed 10%.

Most lipids may be constituents of MPVs. Suitable hydrophilic groups include but are not limited to: phosphato, carboxylic, sulphato and amino groups. Suitable hydrophobic groups include but are not limited to: saturated and unsaturated aliphatic hydrocarbon groups and aliphatic hydrocarbon groups substituted by at least one aromatic and/or cycloaliphatic group. The preferred amphipathic compounds are phospholipids and closely related chemical structures.

Specific examples of suitable lipids useful in the production of MPVs are phospholipids which include but are not limited to the natural lecithins or phosphatidylcholines (e.g., egg lecithin or soybean lecithin) and synthetic lecithins, such as saturated synthetic lecithins (e.g., dimyristoylphosphatidylcholine or dipalmitoylphosphatidylcholine or distearoylphosphatidylcholine) and unsaturated synthetic lecithins (e.g., dioleoylphosphatidylcholine or dilinoleoylphosphatidylcholine). Other phospholipids include but are not limited to phosphatidylethonolamine, lysolecithin, lysophosphatidylethanolamine, phosphatidylserine, phosphatidylinositol, sphingomyelin, cardiolipin, phosphatidic acid, ceramides and the cerebrosides. The MPV bilayers can contain a steroid component such as cholesterol, coprostanol, cholestanol, cholestane and the like. When using compounds with acidic hydrophilic groups (phosphato, sulphato, etc.) the obtained MPVs will be anionic; with basic groups such as amino, cationic liposomes will be obtained.

MPVs may advantageously be used in delivery systems wherein a bioactive agent is entrapped within the MPV ("entrapped" is defined as entrapment within the aqueous compartment or within the membrane bilayer). In order to entrap one or more agents in MPVs, the agent or agents may be added to the monophase prior to evaporation and formation of the film. Alternatively, the agent or agents may be added with the aqueous component used to resuspend the film and form the MPVs. In fact, to obtain a high entrapment efficiency, the agent or agents may be added to both the monophase and to the aqueous component used to resuspend the film. Two or more agents can also be entrapped in one MPV preparation by adding one agent to the monophase and the other to the aqueous component used to resuspend the film.

Virtually any bioactive compound can be entrapped within an SPLV or an MPV. Such compounds include but are not limited to nucleic acids, polynucleotides, antibacterial compounds, antiviral compounds, antifungal compounds, anti-parasitic compounds, tumoricidal compounds, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, anti-glaucomic agents, mydriatic compounds, anesthetics, etc.

4.4. THERAPEUTIC USES OF FIBRONECTIN CONJUGATES

The covalently linked fibronectin conjugates of the present invention are particularly well suited for a wide range of applications such as drug delivery or drug carrier systems. The strong affinity of fibronectin for collagen, heparin, hyaluronic acid, fibrin/fibrinogen, and gangliosides permits localization and retention of the FN-conjugates or the FN-modified liposomes. Depending upon the route of administration, retention at a variety of collagen rich body sites including skin, bone, tendon, cartilage, blood vessels, teeth and ocular tissues (especially conjunctiva and cornea) can be accomplished.

Some uses of the fibronectin conjugates are described below but do not limit the scope of the present invention.

Localized delivery of anti-inflammatory and/or analgesic agents including but not limited to aspirin, indomethacin, ibuprofen, flurbiprofen pinoxicam, naproxen, prednisolone, dexamethasone, cortisone, cortisol, as well as therapeutic gold compounds can be achieved by practice of the present invention employing fibronectin conjugates incorporated into liposome preparations which are then injected directly into joints. Such localization is particularly advantageous in that the therapeutic agent is slowly released into collagen-rich joints where needed and undesirable systemic effects particularly those seen with steroidal hormones are avoided. Inflammation of joints due to rheumatoid arthritis or traumatic injury may thus be treated. Sustained release from adherent liposomes is especially advantageous in obviating repeated injections into joints in conditions where prolonged therapy is anticipated.

Fibronectin conjugates of the present invention may also be employed to treat ocular afflictions. Adherence of fibronectin conjugates (applied directly as FN-conjugates or as FN-liposomes) to collagenous surfaces of the cornea and conjunctiva will retard flushing of drug from the eye and permit sustained delivery of medicament to localized site. Ocular conditions which may thus be treated include but are not limited to: glaucoma, dry eye, and infections ("pink-eye"). A number of organisms cause eye infections in man and animals. Such organisms include but are not limited to: *Moraxella spp., Clostridia spp., Corynebacteria spp., Diplococcus spp., Leptospira spp., Mycobacteria spp., Neisseria spp., Propionibacteria spp., Proteus spp., Pseudomonas spp., Serratia spp., Escherichia spp., Staphylococcus spp., Streptococcus spp.*, and bacteria-like organisms including *Mycoplasma spp., Chlamydia spp.*, and *Rickettsia spp.* Most recent evidence has shown that ocular application of fibronectin has been effective in treating recurrent corneal erosion (Nishida et al., The Lancet, Aug. 27, 1983 pp. 521–522).

Another area in which fibronectin conjugates may be used with advantage is the treatment of both accidentally inflicted and surgical wounds in which collagenous fibers of tissues are particularly exposed. Topical application of fibronectin conjugated with antimicrobial agents especially antibiotics and antifungals (or fibronectin conjugated to liposomes containing the antimicrobial agent) may permit adherence of the active agent at vulnerable sites for both prevention and treatment of wound infections.

Because fibronectin conjugates injected intraperitoneally adhere especially to the body cavity, such administration of fibronectin-antimicrobial conjugates may be used to prevent and/or treat conditions such as peritonitis.

Intramammary infusion of fibronectin conjugates may have particular application for treatment of conditions such as mastitis in cows, goats or other milk producing animals.

4.4.1. METHODS OF ADMINISTRATION

The present invention encompasses fibronectin conjugated with either free drug or materials incorporated into a liposome bilayer immobilized at specific body sites by a variety of routes of administration. In man and animals drugs or drug-carrier complexes may be administered by a number of routes including but not limited to: injection (e.g., intravenous, intrathecal, intraperitoneal, intramuscular, subcutaneous, intraarticular, intramammary, intraurethral, etc.); topical application (e.g., on afflicted areas); and by absorption through epithelial or mucocutaneous linings (e.g., ocular epithelia, oral mucosa, rectal and vaginal epithelial linings, the respiratory tract linings, nasopharyngeal mucosa, intestinal mucosa, etc.).

The mode of application may also determine the sites and cells in the organism to which the compound will be delivered. For instance, delivery to a specific site of infection may be most easily accomplished by topical application (if the infection is external). Adherence of medicament or medicament-carrier complex at the infection site provides delivery of active compound where needed and avoids possible untoward systemic effects of active compound. Alternatively, delivery to the circulatory system may be most easily accomplished by intravenous, intraperitoneal, intramuscular, or subcutaneous injections.

The following example is given for purposes of illustration and not by way of limitation on the scope of the invention.

5. EXAMPLE: INTRA-ARTICULAR ADMINISTRATION FOR LOCALIZED DELIVERY TO JOINTS

In this example, fibronectin covalently linked to SPLVs provides sustained release of anti-inflammatory drug when administered intra-articularly in mice. Fibronectin-modified SPLVs injected into joints adhered to joint and associated tissues at significant concentrations for at least 24 hours. Release of entrapped anti-inflammatory drug from adherent SPLVs was demonstrated.

For this example control SPLVs were prepared as described in Section 4.3. using the following formulation: 100 mg EPC, 3.7 mg PE, and 10 mg indomethacin were dissolved in chloroform and then dried down to a film. The indomethacin was entrapped in the SPLVs by resuspending the film in ether, adding the aqueous phase and sonicating while evaporating. Trace amounts of radiolabeled $^{14}C$-indomethacin were incorporated to quantify retention of drug in joints of injected test animals.

Twenty-five female Swiss Webster mice were anesthetized with 50 mg/kg pentobarbitol and divided into 5 treatment groups. Group 1 was treated with unentrapped $^{14}C$-indomethacin (trace amount) in PBS buffer solution. Group 2 was treated with $^{14}C$-indomethacin entrapped in SPLVs (control SPLVs). Group 3 was treated with fibronectin-modified control SPLVs (non-covalent association) prepared by incubation of the SPLV-entrapped $^{14}C$-indomethacin with 0.3 mg fibronectin (FN, Seragen, Inc., Boston, Mass.; or Collaborative Research, Inc., Lexington, Mass.) for 2 hours before the SPLVs were repeatedly washed to remove unincorporated materials. Groups 4 and 5 were treated with SPLVs in which fibronectin was covalently attached to the liposomes. Group 4 SPLVs were prepared using control SPLVs which were incubated with 0.3 mg FN and 100 ug Factor XIII (transglutaminase, Alpha Therapeutic Corp., Los Angeles, Calif.) in PBS buffer containing 20 mM $CaCl_2 \cdot 6H_2O$. Group 5 SPLVs were prepared as were the SPLVs of Group 4 except 1 unit thrombin (Sigma, St. Louis, Mo.), a known activator of Factor XIII, was included in the reaction mixture. In all cases the femoral-tibia articulation of anesthetized test animals was injected with a total volume of 2 ul test sample. At 5 or 24 hours post-injection, animals were sacrificed, the treated joints were removed, minced and digested in 1.5 ml Protosol (New England Nuclear, Boston, Mass.). Sealed sample tubes were incubated for 2 days at 37° C. After digestion the samples were decolorized by addition of 0.25 ml of 20% benzoyl peroxide and 0.02 ml of 30% $H_2O_2$. Two drops of glacial acetic acid were then added and samples were dark adapted over night before radioactivity was determined.

Results illustrated in Table II expressed as % total radioactivity remaining in the joints (cpm recovered divided by the total cpm injected into the joint expressed as percent) indicate that encapsulation of drug in liposome vesicles dramatically enhanced retention of indomethacin in femoral-tibia articulation. Furthermore, when fibronectin was covalently bound to the lipid bilayer of the SPLVs injected (groups 4 and 5) the joints retained approximately 20 times and 5 times the amount of radiolabel (at 5 and 24 hours post injection respectively) measured in joints treated with unentrapped drug (group 1). Covalent linkage of fibronectin to lipid increased retention in joints 5 hours post injection (groups 4 and 5 compared with group 3).

TABLE II
RETENTION OF SPLV-ENCAPSULATED INDOMETHACIN AFTER INTRA-ARTICULAR APPLICATION TO JOINTS OF MICE

| Group No. | Treatment | % Total $^{14}C$-Indomethacin Remaining in Joint[a] | |
|---|---|---|---|
| | | 5 Hours | 24 Hours |
| 1 | Unentrapped $^{14}C$-Indomethacin | 4.7 | 1.0 |
| 2 | Control SPLVs[b] | 28.8 | 1.9 |
| 3 | Control SPLVs + FN[c] | 59.9 | 5.6 |
| 4 | Control SPLVs + FN + Factor XIII[d] | 100.0 | 5.4 |
| 5 | Control SPLVs + FN + Factor XIII + Thrombin[e] | 99.1 | 7.6 |

[a] All values were normalized to maximum possible value of 100%.
[b] SPLVs: 100 mg egg phosphatidylcholine, 3.7 mg phosphatidylethanolamine, and 10 mg indomethacin.
[c] Control SPLVs were incubated with 0.3 mg fibronectin (FN) for 2 hours resulting in a non-covalent association.
[d] Control SPLVs were incubated with 0.3 mg fibronectin in 20 mM $CaCl_2 6 H_2O$ with Factor XIII which covalently links fibronectin to PE.
[e] Thrombin (1 unit) was added to the reaction mixture described in footnote d.

In order to determine whether intact liposome vesicles were adherent to animal joints, the above experiment was repeated except that SPLVs were radiolabeled with $^{125}I$-p-hydroxyphenylpropionic acid derivatized phosphatidylethanolamine as a lipid marker. Methods used were identical to the experiment detailed above in this example, except that digestion of femoral-tibia joints of test animals was not necessary for determination of radioactivity by gamma-emitting radiolabel. Aliquots of minced joints were counted directly. Between 30 to 50% of the lipid was present after 24 hours.

As indicated in Table II, only 6–8% of the entrapped indomethacin remained in treated joints at the end of the 24 hour period. Thus, the indomethacin appeared to diffuse out of adherent SPLVs, thereby affording a sustained release of anti-inflammatory drug to injected joints.

What is claimed is:

1. A lipid vesicle, comprising a lipid bilayer and an entrapped aqueous compartment in which a component of the bilayer comprises a carboxyl-containing lipid directly attached to fibronectin via a peptide bond between a carboxyl group of the lipid and an amino group of the fibronectin, and in which the fibronectin is present in an amount of at least 0.1% by weight of the lipids in the lipid vesicle.

2. The lipid vesicle according to claim 1, wherein the carboxyl-containing lipid is phosphatidylserine.

3. The lipid vesicle according to claim 1, wherein the carboxyl-containing lipid is palmitate.

4. The lipid vesicle according to claim 1, wherein the vesicle is a stable plurilamellar vesicle.

5. The lipid vesicle according to claim 1, wherein the vesicle is a monophasic vesicle.

6. The lipid vesicle according to claim 1, wherein the vesicle is a multilamellar vesicle.

7. The lipid vesicle according to claim 1, wherein the vesicle contains an entrapped bioactive agent.

8. The lipid vesicle according to claim 7, wherein the bioactive agent is an anti-inflammatory.

9. The lipid vesicle according to claim 8, wherein the anti-inflammatory is indomethacin.

10. The lipid vesicle according to claim 7, wherein the bioactive agent is an antimicrobial agent.

11. The lipid vesicle according to claim 10, wherein the antimicrobial agent is an aminoglycoside.

12. The lipid vesicle according to claim 1, wherein the fibronectin comprises from about 0.1% to about 5% by weight of phospholipid in the bilayer.

13. A lipid vesicle, comprising a lipid bilayer and an entrapped aqueous compartment in which a component of the bilayer comprises a amino-containing lipid directly attached to fibronectin via a peptide bond between an amino group of the lipid and a γ-carboxamide group of a glutamyl residue on the N-terminus of the fibronectin, and in which the fibronectin is present in an amount of at least 0.1% by weight of the lipids in the lipid vesicle, and wherein the vesicle is a stable plurilamellar vesicle or a monophasic vesicle.

14. A lipid vesicle, comprising a lipid bilayer and an entrapped aqueous compartment, in which a component of the bilayer comprises a water-insoluble lipid having an amino group that is covalently attached directly, with no intervening groups, to a carboxyl group of the fibronectin.

15. The lipid vesicle according to claim 14, wherein the amino-containing lipid is phosphatidylethanolamine.

16. The lipid vesicle according to claim 14, wherein the amine-containing lipid is phosphatidylserine.

17. The lipid vesicle according to claim 14, wherein the vesicle is a stable plurilamellar vesicle.

18. The lipid vesicle according to claim 14, wherein the vesicle is a monophasic vesicle.

19. The lipid vesicle according to claim 14, wherein the vesicle is a multilamellar vesicle.

20. The lipid vesicle according to claim 14, wherein the vesicle contains an entrapped bioactive agent.

21. The lipid vesicle according to claim 20, wherein the bioactive agent is an anti-inflammatory.

22. The lipid vesicle according to claim 21, wherein the anti-inflammatory is indomethacin.

23. The lipid vesicle according to claim 20, wherein the bioactive agent is an antimicrobial agent.

24. The lipid vesicle according to claim 23, wherein the antimicrobial agent is an aminoglycoside.

25. The lipid vesicle according to claim 14, wherein the fibronectin comprises from about 0.1% to about 5% by weight of phospholipid in the bilayer.

* * * * *